United States Patent
Shimizu et al.

(10) Patent No.: US 7,521,562 B2
(45) Date of Patent: Apr. 21, 2009

(54) FILTERS FOR ELECTRONIC DISPLAY DEVICES

(75) Inventors: Ikuo Shimizu, Tokyo (JP); Junzo Yamano, Mie (JP); Motoharu Kinugasa, Mie (JP); Katsumi Ukai, Mei (JP)

(73) Assignee: Kyowa Hakko Chemical Co., Ltd., Tokyo (JP)

( * ) Notice: Subject to any disclaimer, the term of this patent is extended or adjusted under 35 U.S.C. 154(b) by 109 days.

(21) Appl. No.: 11/570,355

(22) PCT Filed: Jul. 27, 2005

(86) PCT No.: PCT/JP2005/013740

§ 371 (c)(1),
(2), (4) Date: Dec. 11, 2006

(87) PCT Pub. No.: WO2006/011514

PCT Pub. Date: Feb. 2, 2006

(65) Prior Publication Data

US 2007/0260059 A1      Nov. 8, 2007

(30) Foreign Application Priority Data

Jul. 27, 2004    (JP)    ............... 2004-218354

(51) Int. Cl.
*C07D 401/00*    (2006.01)

(52) U.S. Cl. .................................... 546/211

(58) Field of Classification Search ............ None
See application file for complete search history.

(56) References Cited

U.S. PATENT DOCUMENTS

| 2001/0044001 A1 | 11/2001 | Noguchi et al. |
| 2003/0157291 A1 | 8/2003 | Noguchi et al. |
| 2007/0105988 A1 | 5/2007 | Shimizu et al. |

FOREIGN PATENT DOCUMENTS

| JP | 2001-322356 | 11/2001 |
| JP | 2002-234259 | 8/2002 |
| JP | 2002-370451 | 12/2002 |
| JP | 2002-370452 | 12/2002 |
| WO | WO 2005/059608 | 6/2005 |

*Primary Examiner*—Rei-Tsang Shiao
*Assistant Examiner*—Sun Jae Y Loewe
(74) *Attorney, Agent, or Firm*—Fitzpatrick, Cella, Harper & Scinto

(57) ABSTRACT

The present invention provides a filter for electronic display devices, comprising a squarylium compound represented by General Formula (I):

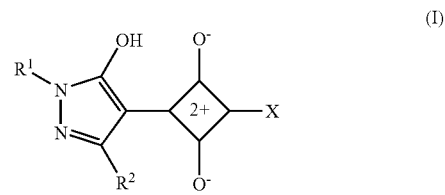

(I)

[wherein $R^1$ and $R^2$ may be the same or different and each represents a hydrogen atom, an alkyl group optionally having substituent(s), an aralkyl group optionally having substituent (s), an aryl group optionally having substituent(s), or a heterocyclic group optionally having substituent(s); X represents a group represented by following Formula (A):

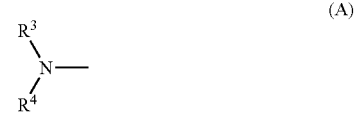

(A)

(wherein $R^3$ and $R^4$ may be the same or different and represents a hydrogen atom, an alkyl group optionally having substituent(s), an alkoxy group optionally having substituent (s), an aralkyl group optionally having substituent(s), an aryl group optionally having substituent(s), or a heterocyclic group optionally having substituent(s), wherein $R^3$ and $R^4$ may be combined together with the adjacent nitrogen atom thereto form a heterocyclic group optionally having substituent(s))].

4 Claims, No Drawings

FILTERS FOR ELECTRONIC DISPLAY DEVICES

TECHNICAL FIELD

The present invention relates to filters for electronic display devices which comprise squarylium compounds.

BACKGROUND ART

Electronic display devices display color images, ideally, by a combination of three primary colors: red, blue, and green. To display images with clearer colors, it has been devised to equip the devices with filters having a color compensating functions.

As coloring compounds for filters having color compensating functions, squarylium compounds have been used for the purpose of selectively shielding the light having a wavelength of 550 to 600 nm (refer to Patent Document 1).

Also, as colorants for an electronic display device filter that can selectively shield the light having a wavelength of 380 to 450 nm, methine colorants are known (refer to Patent Document 2) but there are no example using squarylium colorants.

Patent Document 1: Japanese Published Unexamined Patent Application No. 2004-86133

Patent Document 2: Japanese Published Unexamined Patent Application No. 2002-131530

DISCLOSURE OF INVENTION

Problem to be Solved by the Invention

An object of the present invention is to provide, for example, filters for electronic display devices which improve colors quality of the electronic display devices, etc.

Means for Solving the Problem

The present invention provides the following (1) to (6):

(1) A filter for electronic display devices, comprising a squarylium compound represented by General Formula (I):

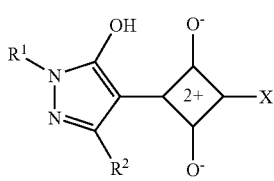

(I)

{wherein $R^1$ and $R^2$ may be the same or different and each represents a hydrogen atom, an alkyl group optionally having substituent(s), an aralkyl group optionally having substituent(s), an aryl group optionally having substituent(s), or a heterocyclic group optionally having substituent(s), wherein X represents a group represented by following Formula (A):

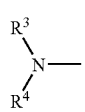

(A)

(wherein $R^3$ and $R^4$ may be the same or different and each represents a hydrogen atom, an alkyl group optionally having substituent(s), an alkoxy group optionally having substituent(s), an aralkyl group optionally having substituent(s), an aryl group optionally having substituent(s), or a heterocyclic group optionally having substituent(s), wherein $R^3$ and $R^4$ may be combined together with the adjacent nitrogen atom thereto to form a heterocyclic group optionally having substituent(s)), or a group represented by following Formula (B):

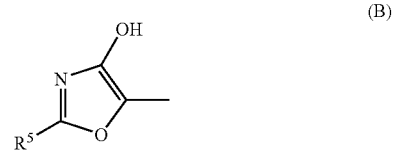

(B)

[wherein $R^5$ represents a hydrogen atom, a halogen atom, a hydroxyl group, an alkyl group optionally having substituent(s), an alkoxy group optionally having substituent(s), an aralkyl group optionally having substituent(s), an aryl group optionally having, substituent(s), —$NR^6R^7$ (wherein $R^6$ and $R^7$ may be the same or different and each represents a hydrogen atom, an alkyl group optionally having substituent(s), an alkoxy group optionally having substituent(s), an aralkyl group optionally having substituent(s), an aryl group optionally having substituent(s), or a heterocyclic group optionally having substituent(s), wherein $R^6$ and $R^7$ may be combined together with the adjacent nitrogen atom thereto to form a heterocyclic group optionally having substituent(s)) or a heterocyclic group optionally having substituent(s)]}.

(2) A filter for electronic display devices comprising a squarylium compound represented by General Formula (Ia):

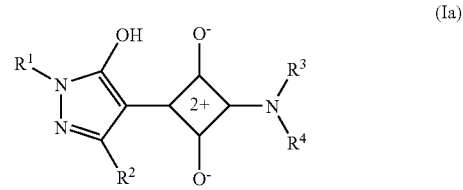

(Ia)

(wherein $R^1$, $R^2$, $R^3$, and $R^4$ have the same definitions as described above, respectively).

(3) A filter for electronic display devices comprising a squarylium compound represented by General Formula (Ib):

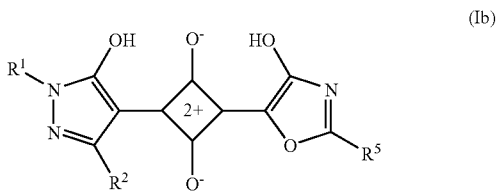

(Ib)

(wherein $R^1$, $R^2$, and $R^5$ have the same definitions as described above, respectively).

(4) The filter for electronic display devices, according to any one of (1) to (3), which has an absorption maximum in a wavelength region of 380 nm to 450 nm (5) A squarylium compound represented by General Formula (Ic):

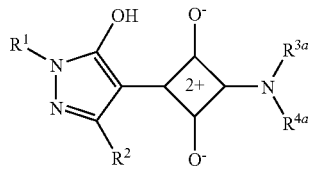

(wherein $R^1$ and $R^2$ have the same definitions as described above, respectively, $R^{3a}$ and $R^{4a}$ may be the same or different and each represents a hydrogen atom, an alkyl group optionally having substituent(s), an alkoxy group optionally having substituent(s), an aralkyl group optionally having substituent(s), or a heterocyclic group optionally having substituent(s), wherein $R^{3a}$ and $R^{4a}$ may be combined together with the adjacent nitrogen atom thereto to form a heterocyclic group optionally having substituent(s)).

(6) A squarylium compound represented by General Formula (Id):

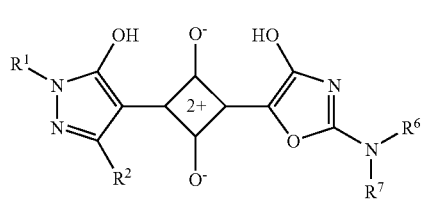

(wherein $R^1$, $R^2$, $R^6$, and $R^7$ have the same definitions as described above, respectively).

Effect of the Invention

The present invention provides, for example, filters for electronic display devices which improve the color quality of the electronic display devices, selectively shield a light having a wavelength of preferably 380 nm to 450 nm and provide clearer images, etc.

BEST MODE FOR CARRYING OUT THE INVENTION

Hereinafter, the compound represented by General Formula (I) is referred to as compound (I). Compounds with other formula numbers are also expressed in the same manner.

In the definition of each group in the general formulae, examples of the alkyl group and an alkyl moiety in the alkoxy group include linear or branched alkyl groups having one to six carbon atoms and cyclic alkyl groups having three to eight carbon atoms, specifically, such as a methyl group, an ethyl group, a propyl group, an isopropyl group, a butyl group, an isobutyl group, a sec-butyl group, a tert-butyl group, a pentyl group, an isopentyl group, a 2-methylbutyl group, a tert-pentyl group, a hexyl group, a cyclopropyl group, a cyclobutyl group, a cyclopentyl group, a cyclohexyl group, a cycloheptyl group, and a cyclooctyl group.

Examples of the aralkyl group include aralkyl groups having seven to fifteen carbon atoms, specifically, such as a benzyl group, a phenethyl group, a phenylpropyl group, and a naphtylmethyl group.

Examples of the aryl group include a phenyl group, a naphthyl group, an anthryl group and the like.

The halogen atom includes a fluorine atom, a chlorine atom, a bromine atom, and an iodine atom.

Examples of a heterocyclic ring in the heterocyclic group include heteroaromatic rings (aromatic heterocyclic rings) and alicyclic heterocyclic rings.

Examples of the heteroaromatic rings include 5- or 6-membered monocyclic heteroaromatic rings containing at least one atom selected from nitrogen atoms, oxygen atoms, and sulfur atoms; fused bicyclic or tricyclic heteroaromatic groups containing at least one atom selected from nitrogen atoms, oxygen atoms, and sulfur atoms wherein 3- to 8-membered rings are fused; and the like. More specific examples thereof are a pyridine ring, a pyrazine ring, a pyrimidine ring, a pyridazine ring, a quinoline ring, an isoquinoline ring, a phthalazine ring, a quinazoline ring, a quinoxaline ring, a naphthyridine ring, a cinnoline ring, a pyrrole ring, a pyrazole ring, an imidazole ring, a triazole ring, a tetrazole ring, a thiophene ring, a furan ring, a thiazole ring, an oxazole ring, an indole ring, an isoindole ring, an indazole ring, a benzimidazole ring, a benzotriazole ring, a benzothiazole ring, a benzoxazole ring, a purine ring, a carbazole ring, and the like.

Examples of the alicyclic heterocyclic rings include 5- or 6-membered monocyclic alicyclic heterocyclic rings containing at least one atom selected from nitrogen atoms, oxygen atoms and sulfur atoms; fused bicyclic or tricyclic alicyclic heterocyclic rings containing at least one atom selected from nitrogen atoms, oxygen atoms and sulfur atoms wherein 3- to 8-membered rings are fused; and the like. More specific examples thereof are pyrrolidine ring, piperidine ring, piperazine ring, morpholine ring, thiomorpholine ring, homopiperidine ring, homopiperazine ring, tetrahydropyridine ring, tetrahydroquinoline ring, tetrahydroisoquinoline ring, tetrahydrofuran ring, tetrahydropyran ring, dihydrobenzofuran ring, tetrahydrocarbazole ring, and the like.

Examples of the heterocyclic ring in heterocyclic group wherein $R^3$ and $R^4$, $R^6$ and $R^7$ or $R^{3a}$ and $R^{4a}$ are combined together with the adjacent nitrogen atoms thereto, include, for example, 5- or 6-membered monocyclic heterocyclic rings containing at least one nitrogen atom (wherein the monocyclic heterocyclic rings may further contain another nitrogen atom, an oxygen atom, or a sulfur atom); fused bicyclic or tricyclic heterocyclic rings containing at least one nitrogen atom, wherein 3- to 8-membered rings are fused (wherein the fused heterocyclic rings may further contain another nitrogen atom, an oxygen atom, or a sulfur atom); and the like. More specific examples thereof are a pyrrolidine ring, a piperidine ring, a piperazine ring, a morpholine ring, a thiomorpholine ring, a homopiperidine ring, a homopiperazine ring, a tetrahydropyridine ring, a tetrahydroquinoline ring, a tetrahydroisoquinoline ring, a pyrrole ring, an imidazole ring, a pyrazole ring, an indole ring, an indoline ring, an isoindole ring and the like.

Substituents of the alkyl group and the alkoxy group may each have, for example, one to three substituents which may be the same or different. Specific examples of the substituents include a hydroxyl group, a carboxyl group, a halogen atom, an alkoxy group, an alkoxyalkoxy group and the like. The halogen atom and the alkoxy group have the same definitions as described above, respectively. The alkoxy moieties of the alkoxyalkoxy group have the same definitions as the above alkoxy and the alkylene moieties are the group formed by removing one hydrogen atom from the above alkoxy.

Substituents of the aralkyl group, the aryl group, the heterocyclic group, the heterocyclic group formed by combining $R^3$ and $R^4$, $R^6$ and $R^7$, or $R^{3a}$ and $R^{4a}$ together with the adjacent nitrogen atoms are, for example, one to five substituents which may be the same or different. Specific examples of the substituents are a hydroxyl group, a carboxyl group, a halogen atom thereto, an alkyl group, an alkoxy group, a nitro group, an amino group optionally having substituent(s), and the like. The halogen atom, the alkyl group and the alkoxy group have the same definitions as described above, respectively. Examples of substituents of the amino group include one or two substituent(s) which may be the same or different, such as an alkyl group, an alkoxy group, an aralkyl group, and an aryl group. The alkyl group, the alkoxy group, the aralkyl group, and the aryl group are as described above, respectively.

Compounds (I) can be prepared in a similar manner to a known method (e.g., WO 01/44233 and the like).

For example, compound (Ia) and compound (Id) can be prepared in the following manner.

Reaction Scheme (1-a)

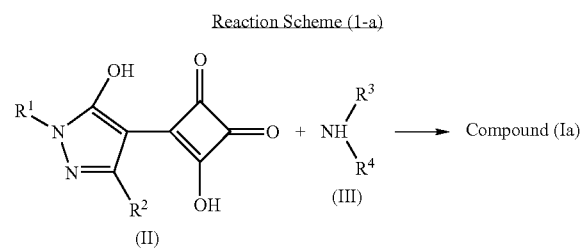

Reaction Scheme (1-b)

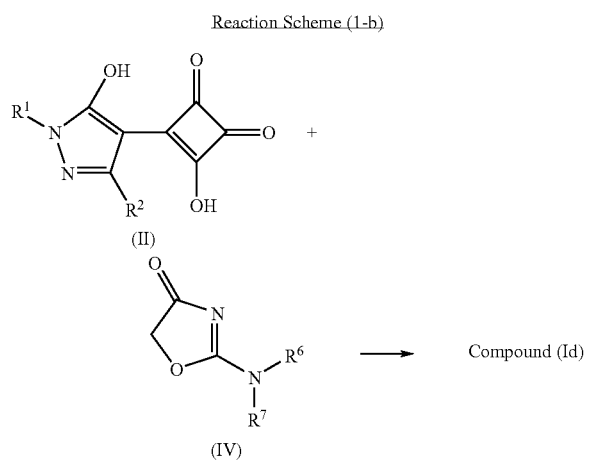

(wherein $R^1$, $R^2$, $R^3$, $R^4$, $R^6$, and $R^7$ have the same definitions as described above, respectively).

Reaction Scheme (1-a)

The compound (II) can be prepared in a similar manner to a known method (e.g., WO 01/44233 and the like).

The compound (Ia) can be obtained by reacting the compound (II) with 1- to 5-fold moles of the compound (III) at a temperature of 80° C. to 120° C. for one to fifteen hours in a solvent.

Examples of the solvent include an alcohol solvent such as ethanol, propanol, isopropyl alcohol, butanol, or octanol; a mixed solvent of the alcohol solvent with benzene, toluene, or xylene, which the mixed solvent contains 50 percent by volume or more of the alcohol solvent; and the like.

After the reaction, if necessary, the desired compound may be purified by a procedure generally used in synthetic organic chemistry (such as column chromatography, recrystallization, or washing with a solvent and the like).

Reaction Scheme (1-b)

The compound (IV) can be prepared in a similar manner to a known method (e.g., J. Org. Chem., 27, 1679 (1962) and the like).

The compound (Id) can be prepared by reacting the compound (II) with 1- to 5-fold moles of the compound (IV) at a temperature of 80° C. to 120° C. for one to fifteen hours in a solvent.

Examples of the solvent include an alcohol solvent such as ethanol, propanol, isopropyl alcohol, butanol, or octanol; a mixed solvent of the alcohol solvent with benzene, toluene, or xylene, which the mixed solvent contains 50 percent by volume or more of the alcohol solvent; and the like.

After the reaction, if necessary, the target compound may be purified by a procedure generally used in synthetic organic chemistry (such as column chromatography, recrystallization, or washing with a solvent).

Preferred examples of the compound (I) are illustrated below. In the structural formulae of Compounds 1 to 17, Me represents a methyl group; Pr represents a propyl group; and Ph represents a phenyl group.

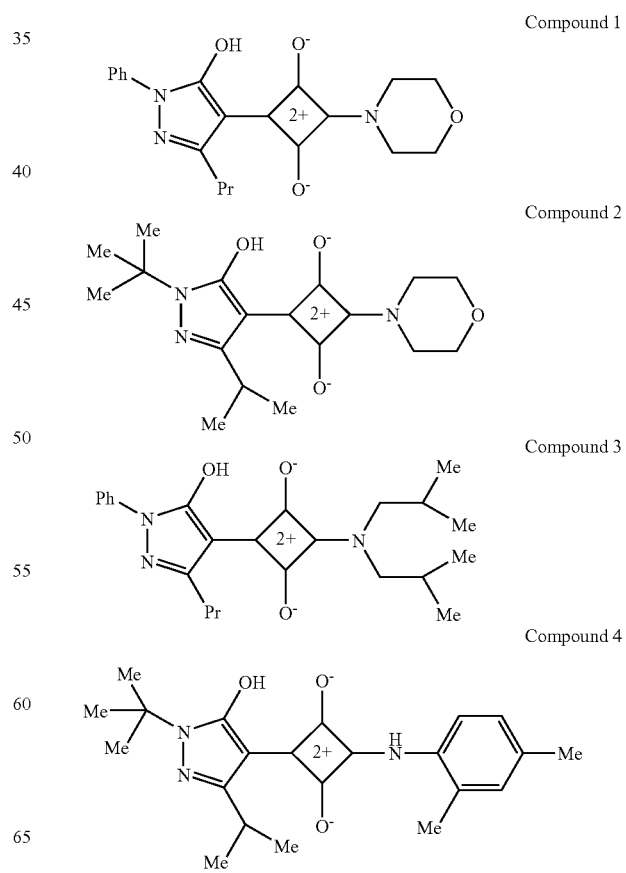

-continued

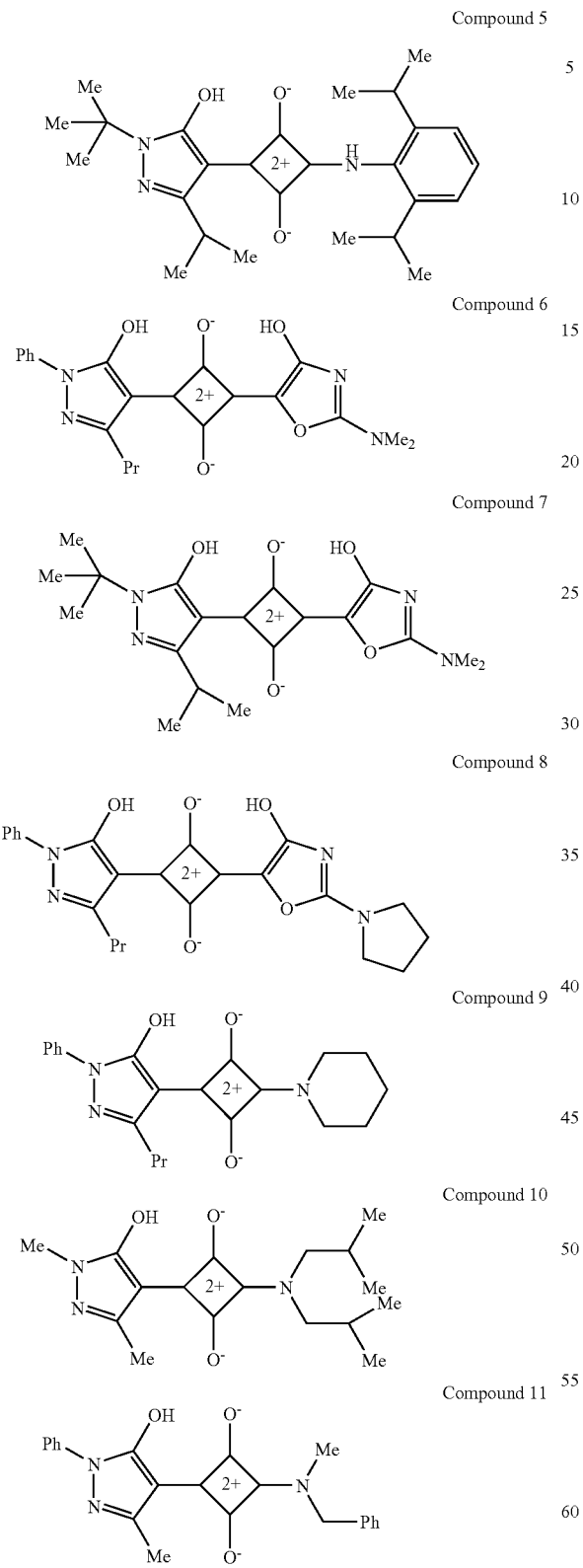

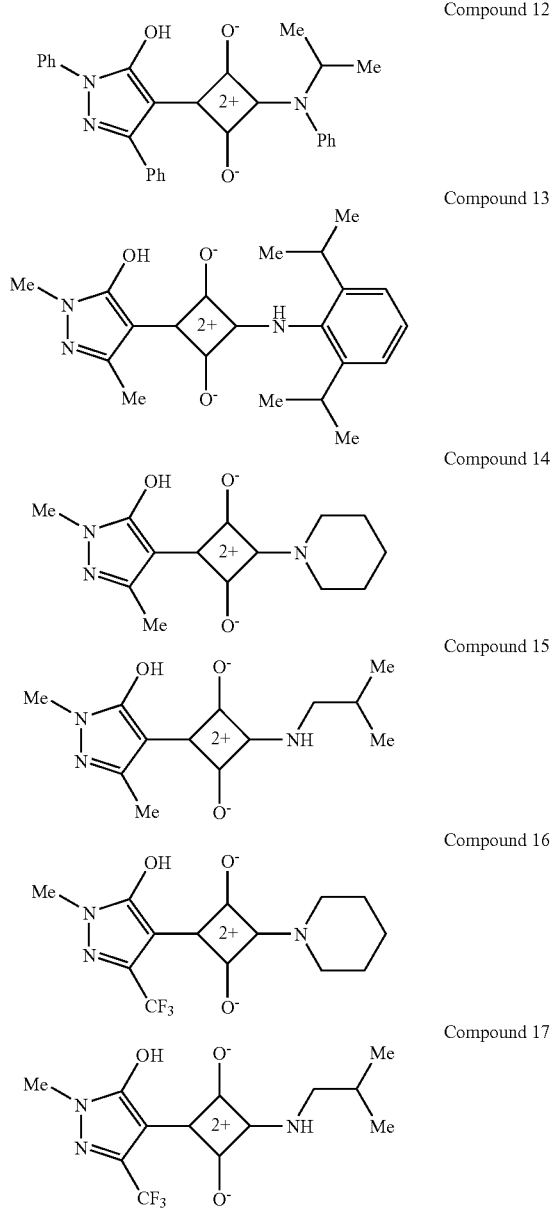

The Compound (I) used as filter for electronic display devices of the present invention can be used as colorant of filter for electronic display devices, colorant of two-photon absorption as three-dimensional recording material, recording material for blue laser and the like. Among them, it is suitable for filter for electronic display devices wherein the half maximum full-width in absorption maximum wavelength region is narrow.

Next, the filter for electronic display devices of the present invention will be illustrated.

Examples of the electronic display devices include liquid crystal displays, plasma displays, organic electroluminescence displays, field emission displays and the like. Among them, plasma displays and the like are preferred.

The compound (I) used for the filter for electronic display devices of the present invention preferably has an absorption maximum in an absorption region of 380 nm to 450 nm in a chloroform solvent, more preferably, an absorption maximum in an absorption region of 380 nm to 420 nm. The compound (I) also preferably has logarithm of a molar extinction coefficient of 4.5 or more, and more preferably 4.7 or more.

The filter for electronic display devices of the present invention preferably has an absorption maximum in an absorption region of 380 to 450 nm, more preferably, an absorption maximum in an absorption region of 380 nm to 420 nm.

The filter for electronic display devices of the present invention is preferably produced by applying a coating composition containing the compound (I) to an optically transparent substrate, and evaporating an organic solvent. If necessary, another optically transparent substrate may be laminated.

The coating composition may be prepared by dissolving a solution of an organic solvent containing the compound (I) with a binder in the organic solvent.

Examples of the organic solvent include ethers such as dimethoxyethane, methoxyethoxyethane, tetrahydrofuran, and dioxane; ketones such as acetone, methyl ethyl ketone, methyl isobutyl ketone, and cyclohexanone; and aromatic hydrocarbons such as benzene, toluene, xylene, and monochlorobenzene; and the like. These organic solvents are preferably used in an amount 10 to 3000-fold by weight to the compound (I).

Examples of the binder include a polyester resin, a polycarbonate resin, a polyacrylic acid resin, a polystyrene resin, a poly(vinyl chloride) resin, a poly(vinyl acetate) resin and the like. The binder is preferably used in an amount 10- to 500-fold by weight to the compound (I).

The optically transparent substrate is not specifically limited, as long as it comprises an optically transparent resin or glass having low absorption and scattering. Examples of the resin include a polyester resin, a polycarbonate resin, a poly(acrylic acid) resin, a polystyrenic resin, a poly(vinyl chloride) resin, a poly(vinyl acetate) resin and the like.

The coating composition containing the compound (I) can be applied to the optically transparent substrate according to a known coating procedure, such as bar coating, spraying, roll coating, or dipping (e.g., U.S. Pat. No. 2,681,294 and the like).

The compound (I) has a high solubility in an organic solvent and is suitable for a method of preparing a filter for electronic display devices using the above coating composition.

The filter for electronic display devices of the present invention may also be prepared by directly dissolving or dispersing the compound (I) in a resin constituting an optically transparent substrate, forming the solution or dispersion into a film, and, if necessary, laminating the film with other optically transparent substrates at one or both sides thereof.

The film formed from the compound (I) preferably has a half maximum full-width (a width of wavelength region indicating half of the absorbance in an absorption maximum wavelength) of 80 nm or less in an absorption maximum wavelength. The film formed from the compound (I) also preferably has a sufficient transmittance in a region of 455 to 465 nm. For example, in the case of the compound (I) having an absorption maximum in a region of 380 to 420 nm, the resulting film preferably has a transmittance of 70% or more at 445 to 465 nm, and more preferably 80% or more.

The filter for electronic display devices according to the present invention can selectively shield the light having such a wavelength that reduces the color purity while maintaining the brightness in visible field (can reduce tinting caused by extra blue lights) and is excellent in the color correcting compensating function. Therefore, the filter can provide clear images excellent in colors.

The filter for electronic display devices of the present invention can be used for, for example, cathode-ray tubes, fluorescent display tubes, electroluminescence panels, light emitting diodes, plasma display panels, incandescent lamps, laser displays, liquid crystal displays, electrochromic displays, field emission displays, and the like.

The present invention will be illustrated in further detail with reference to the following Examples, Reference Examples, and Test Example.

EXAMPLE 1

Preparation of Compound 1

Starting material 3-hydroxy-4-[(5-hydroxy-1-phenyl-3-propyl)pyrazol-4-yl]cyclobutene-1,2-dione was synthesized in a similar manner to the method described in WO 01/44233.

To a mixed solvent of 3 ml of butanol and 3 ml of toluene, 1.00 g of 3-hydroxy-4-[(5-hydroxy-1-phenyl-3-porpyl)pyrazol-4-yl]cyclobutene-1,2-dione and 0.41 g of morpholine were added, and the mixture was reacted at 100° C. to 110° C. for 2.5 hours. Then, 3 ml of methanol was added to the reaction mixture and the mixture was cooled to 20° C. to 30° C., and the precipitated yellow solid was collected by filtration to obtain Compound 1 (0.74 g).

$^1$H-NMR (CDCl$_3$) δppm: 1.01-1.04 (3H, t, J=7.2 Hz), 1.69-1.78 (2H, m), 2.87-2.91 (2H, t, J=8.0 Hz), 3.89-3.92 (4H, t, J=4.8 Hz), 4.02 (2H, br), 4.14 (2H, br), 7.26-7.30 (1H, m), 7.41-7.46 (2H, m), 7.78-7.81 (2H, m).

EXAMPLE 2

Preparation of Compound 2

Starting material 3-hydroxy-4-[(1-tert-butyl-5-hydroxy-3-isopropyl)pyrazol-4-yl]cyclobutene-1,2-dione was synthesized in a similar manner to the method described in WO 01/44233.

To a mixed solvent of 1 ml of butanol and 1 ml of toluene, 0.50 g of 3-hydroxy-4-[(1-tert-butyl-5-hydroxy-3-isopropyl)pyrazol-4-yl]cyclobutene-1,2-dione and 0.20 g of morpholine were added and the mixture was reacted at 100° C. to 110° C. for 4.0 hours. Then, 1 ml of methanol was added to the reaction mixture and the mixture was cooled to 0° C. to 5° C. The precipitated yellow solid was collected by filtration to obtain Compound 2 (0.14 g).

$^1$H-NMR (CDCl$_3$) δppm: 1.23-1.25 (6H, d, J=6.8 Hz), 1.56 (9H, s), 3.43-3.50 (1H, m), 3.87-3.89 (4H, t, J=5.2 Hz), 3.99 (2H, br), 4.11 (2H, br), 13.63 (1H, br).

EXAMPLE 3

Preparation of Compound 3

Starting material 3-hydroxy-4-[(5-hydroxy-1-phenyl-3-propyl)pyrazol-4-yl]cyclobutene-1,2-dione was synthesized in a similar manner to the method described in WO 01/44233.

To a mixed solvent of 1 ml of butanol and 1 ml of toluene, 0.5 g of 3-hydroxy-4-[(5-hydroxy-1-phenyl-3-propyl)pyrazol-4-yl]cyclobutene-1,2-dione and 0.30 g of diisobutylamine were added and the mixture was reacted at 100° C. to 110° C. for 10.5 hours. Then, 1 ml of methanol and 0.5 ml of hexane were added to the reaction mixture and the mixture was cooled to 0° C. to 5° C. The precipitated yellow solid was collected by filtration to obtain Compound 3 (0.15 g).

$^1$H-NMR (CDCl$_3$) δppm: 1.00-1.02 (12H, d, J=6.8 Hz), 1.01-1.04 (3H, t, J=7.2 Hz), 1.71-1.80 (2H, m), 2.05-2.15 (2H, m), 2.90-2.94 (2H, t, J=7.2 Hz), 3.60-3.62 (2H, d, J=7.6 Hz), 3.71-3.73 (2H, d, J=7.6 Hz), 7.24-7.29 (1H, m), 7.40-7.45 (2H, m), 7.78-7.81 (2H, m).

EXAMPLE 4

Preparation of Compound 4

Starting material 3-hydroxy-4-[(1-tert-butyl-5-hydroxy-3-isopropyl)pyrazol-4-yl]cyclobutene-1,2-dione was synthesized in a similar manner to the method described in WO 01/44233.

To a mixed solvent of 0.5 ml of butanol and 0.5 ml of toluene, 0.30 g of 3-hydroxy-4-[(1-tert-butyl-5-hydroxy-3-isopropyl)pyrazol-4-yl]cyclobutene-1,2-dione and 0.17 g of 2,4-xylidine were added and the mixture was reacted at 100° C. to 110° C. for 6.0 hours. Then, 1 ml of methanol was added to the reaction mixture and the mixture was cooled to 0° C. to 5° C. The precipitated yellow solid was collected by filtration to obtain Compound 4 (0.25 g).

EXAMPLE 5

Preparation of Compound 5

Starting material 3-hydroxy-4-[(1-tert-butyl-5-hydroxy-3-isopropyl)pyrazol-4-yl]cyclobutene-1,2-dione was synthesized in a similar manner to the method described in WO 01/44233.

To a mixed solvent of 0.5 ml of butanol and 0.5 ml of toluene, 0.50 g of 3-hydroxy-4-[(1-tert-butyl-5-hydroxy-3-isopropyl)pyrazol-4-yl]cyclobutene-1,2-dione and 0.41 g of 2,6-diisopropylaniline were added and the mixture was reacted at 100° C. to 110° C. for 7.0 hours. Then, 1 ml of methanol was added to the reaction mixture and the mixture was cooled to 20° C. to 30° C. The precipitated yellow solid was collected by filtration to obtain Compound 5 (0.32 g).

$^1$H-NMR (CDCl$_3$) δppm: 0.99-1.00 (6H, d, J=6.8 Hz), 1.25-1.26 (12H, d, J=6.8 Hz), 1.50 (9H, s), 3.14-3.20 (2H, m), 3.28-3.34 (1H, m), 7.22-7.27 (2H, d, J=7.6 Hz), 7.37-7.41 (1H, t, J=7.6 Hz), 11.37 (1H, br), 13.58 (1H, br).

EXAMPLE 6

Preparation of Compound 6

Starting material 3-hydroxy-4-[(5-hydroxy-1-phenyl-3-propyl)pyrazol-4-yl]cyclobutene-1,2-dione was synthesized in a similar manner to the method described in WO 01/44233. Also, starting material 2-dimethylamino-2-oxazolin-4-one was synthesized in a similar manner to the method described in J. Org. Chem., 27, 1679 (1962).

To a mixed solvent of 10 ml of butanol and 10 ml of toluene, 0.50 g of 3-hydroxy-4-[(5-hydroxy-1-phenyl-3-propyl)pyrazol-4-yl]cyclobutene-1,2-dione and 0.30 g of 2-dimethylamino-2-oxazolin-4-one were added, and the mixture was reacted at 100° C. to 110° C. for 10.5 hours. The reaction mixture was then cooled to 20° C. to 30° C., and the precipitated orange solid was collected by filtration to obtain Compound 6 (0.18 g).

$^1$H-NMR (CDCl$_3$) δppm: 1.00-1.04 (3H, t, J=7.6 Hz), 1.69-1.78 (2H, m), 2.88-2.92 (2H, t, J=7.6 Hz), 3.48 (3H, br), 3.55 (3H, br), 7.25-7.29 (1H, m), 7.40-7.45 (2H, m), 7.78-7.81 (2H, m).

EXAMPLE 7

Preparation of Compound 7

Starting material 3-hydroxy-4-[(1-tert-butyl-5-hydroxy-3-isopropyl)pyrazol-4-yl]cyclobutene-1,2-dione was synthesized in a similar manner to the method described in WO 01/44233. Also, starting material 2-dimethylamino-2-oxazolin-4-one was synthesized in a similar manner to the method described in J. Org. Chem., 27, 1679 (1962).

To a mixed solvent of 10 ml of butanol and 10 ml of toluene, 0.59 g of 3-hydroxy-4-[(1-tert-butyl-5-hydroxy-3-isopropyl)pyrazol-4-yl]cyclobutene-1,2-dione and 0.30 g of 2-dimethylamino-2-oxazolin-4-one were added and the mixture was reacted at 100° C. to 110° C. for 8.5 hours. The reaction mixture was concentrated, added with 2 ml of methanol and then heated at 75° C. for 30 minutes. The precipitated yellow solid was collected by filtration to obtain Compound 7 (0.05 g).

$^1$H-NMR (CDCl$_3$) δppm: 1.23-1.25 (6H, d, J=6.8 Hz), 1.56 (9H, s), 3.45 (3H, br), 3.45-3.52 (1H, m), 3.52 (3H, br), 13.61 (1H, br).

EXAMPLE 8

Preparation of Compound 8

Starting material 3-hydroxy-4-[(5-hydroxy-1-phenyl-3-propyl)pyrazol-4-yl]cyclobutene-1,2-dione was synthesized in a similar manner to the method described in WO 01/44233. Also, starting material 2-pyrrolidino-2-oxazolin-4-one was synthesized in a similar manner to the method described in J. Org. Chem., 27, 1679 (1962).

To a mixed solvent of 10 ml of butanol and 10 ml of toluene, 0.50 g of 3-hydroxy-4-[(5-hydroxy-1-phenyl-3-propyl)pyrazol-4-yl]cyclobutene-1,2-dione and 0.39 g of 2-pyrrolidino-2-oxazolin-4-one were added and the mixture was reacted at 100° C. to 110° C. for 5.0 hours. Then, 10 ml of methanol was added to the reaction mixture and the mixture was cooled to 0° C. to 5° C. The precipitated yellow solid was collected by filtration to obtain Compound 8 (0.12 g).

$^1$H-NMR (CDCl$_3$) δppm: 1.01-1.04 (3H, t, J=7.6 Hz), 1.69-1.79 (2H, m), 2.06-2.09 (4H, m), 2.88-2.92 (2H, t, J=7.6 Hz), 4.01 (4H, br), 7.25-7.29 (1H, t, J=7.6 Hz), 7.41-7.45 (2H, t, J=7.6 Hz), 7.79-7.81 (2H, d, J=7.6 Hz).

EXAMPLE 9

Preparation of Compound 9

Starting material 3-hydroxy-4-[(5-hydroxy-1-phenyl-3-propyl)pyrazol-4-yl]cyclobutene-1,2-dione was synthesized in a similar manner to the method described in WO 01/44233.

To a mixed solvent of 1 ml of butanol and 1 ml of toluene, 0.50 g of 3-hydroxy-4-[(5-hydroxy-1-phenyl-3-propyl)pyrazol-4-yl]cyclobutene-1,2-dione and 0.19 g of piperidine were added and the mixture was reacted at 100° C. to 110° C. for 5.5 hours. Then, 1 ml of methanol was added to the reaction mixture and the mixture was cooled to 20° C. to 30° C. The precipitated yellow solid was collected by filtration to obtain Compound 9 (0.34 g).

$^1$H-NMR (CDCl$_3$) δppm: 1.01-1.05 (3H, t, J=7.6 Hz), 1.69-1.79 (4H, m), 1.81-1.86 (4H, m), 2.89-2.93 (2H, t, J=7.6 Hz), 4.00 (4H, br), 7.23-7.27 (1H, m), 7.39-7.44 (2H, m), 7.80-7.83 (2H, m).

EXAMPLE 10

Preparation of Compound 10

Starting material 3-hydroxy-4-[(1,3-dimethyl-5-hydroxy)pyrazol-4-yl]cyclobutene-1,2-dione was synthesized in a similar manner to the method described in WO 01/44233.

To a mixed solvent of 6 ml of butanol and 6 ml of toluene, 3.00 g of 3-hydroxy-4-[(1,3-dimethyl-5-hydroxy)pyrazol-4-yl]cyclobutene-1,2-dione and 2.55 g of diisobutylamine were added and the mixture was reacted at 100° C. to 110° C. for 7.0 hours. The reaction mixture was concentrated, added with 8 ml of methanol and heated at 75° C. for 30 minutes. Then, the mixture was cooled to 0° C. to 5° C. and the precipitated yellow solid was collected by filtration to obtain Compound 10 (1.06 g).

$^1$H-NMR (CDCl$_3$) δppm: 0.99-1.00 (12H, t, J=7.6 Hz), 2.05-2.12 (2H, m), 2.45 (3H, s), 3.54 (3H, s), 3.58-3.60 (2H, d, J=7.2 Hz), 3.68-3.70 (2H, d, J=7.2 Hz).

EXAMPLE 11

Preparation of Compound 11

Starting material 3-hydroxy-4-[(5-hydroxy-1-phenyl-3-propyl)pyrazol-4-yl]cyclobutene-1,2-dione was synthesized in a similar manner to the method described in WO 01/44233.

To a mixed solvent of 2 ml of butanol and 2 ml of toluene, 3.00 g of 3-hydroxy-4-[(5-hydroxy-1-phenyl-3-propyl)pyrazol-4-yl]cyclobutene-1,2-dione and 1.58 g of N-benzylmethylamine were added and the mixture was reacted at 100° C. to 110° C. for 5.0 hours. Then, 8 ml of methanol was added to the reaction mixture and the mixture was cooled to 0° C. to 5° C. The precipitated yellow solid was collected by filtration to obtain Compound 11 (2.35 g).

$^1$H-NMR (DMSO-d$_6$) δppm: 0.93-0.97 (3H, t, J=7.6 Hz), 1.63-1.69 (2H, m), 2.79-2.83 (2H, t, J=7.6 Hz), 3.32 (3H, s), 5.00 (2H, s), 7.31-7.35 (1H, t, J=7.6 Hz), 7.41-7.51 (7H, m), 7.74-7.77 (2H, m).

EXAMPLE 12

Preparation of Compound 12

Starting material 3-hydroxy-4-[(1,3-diphenyl-5-hydroxy)pyrazol-4-yl]cyclobutene-1,2-dione was synthesized in a similar manner to the method described in WO 01/44233.

To a mixed solvent of 5 ml of butanol and 5 ml of toluene, 2.00 g of 3-hydroxy-4-[(1,3-diphenyl-5-hydroxy)pyrazol-4-yl]cyclobutene-1,2-dione and 1.22 g of N-isopropylaniline were added and the mixture was reacted at 100° C. to 110° C. for 6.5 hours. Then, 10 ml of methanol was added to the reaction mixture and the mixture was cooled to 20° C. to 30° C. The precipitated yellow-green solid was collected by filtration to obtain Compound 12 (2.19 g).

$^1$H-NMR (DMSO-d$_6$) δppm: 1.30-1.32 (6H, d, J=7.6 Hz), 5.02-5.09 (1H, m), 7.34-7.83 (15H, m).

EXAMPLE 13

Preparation of Compound 13

Starting material 3-hydroxy-4-[(1,3-dimethyl-5-hydroxy)pyrazol-4-yl]cyclobutene-1,2-dione was synthesized in a similar manner to the method described in WO 01/44233.

To a mixed solvent of 10 ml of butanol and 5 ml of toluene, 2.08 g of 3-hydroxy-4-[(1,3-dimethyl-5-hydroxy)pyrazol-4-yl]cyclobutene-1,2-dione and 2.12 g of 2,6-diisopropylaniline were added and the mixture was reacted at 100° C. to 110° C. for 7.0 hours. The reaction mixture was concentrated, added with 5 ml of methanol and then heated at 75° C. for 1 hour. The mixture was cooled to 20° C. to 30° C. and the precipitated yellow solid was collected by filtration to obtain Compound 13 (1.76 g).

$^1$H-NMR (CDCl$_3$) δppm: 1.23-1.26 (12H, d, J=6.8 Hz), 2.31 (3H, s), 3.13-3.16 (2H, br), 3.49 (1H, t, J=6.8), 7.24-7.29 (1H, d, J=7.8 Hz), 7.40-7.45 (2H, d, J=7.6 Hz).

EXAMPLE 14

Preparation of Compound 14

Starting material 3-hydroxy-4-[(1,3-dimethyl-5-hydroxy)pyrazol-4-yl]cyclobutene-1,2-dione was synthesized in a similar manner to the method described in WO 01/44233.

To a mixed solvent of 4 ml of butanol and 2 ml of toluene, 2.08 g of 3-hydroxy-4-[(1,3-dimethyl-5-hydroxy)pyrazol-4-yl]cyclobutene-1,2-dione and 1.04 g of piperidine were added and the mixture was reacted at 100° C. to 110° C. for 8.0 hours. Then, 5 ml of methanol and 5 ml of diisopropylether was added to the reaction mixture and the mixture was cooled to 20° C. to 30° C. The precipitated yellow solid was collected by filtration to obtain Compound 14 (1.59 g).

$^1$H-NMR (CDCl$_3$) δppm: 1.71-1.86 (6H, m), 2.44 (3H, s), 3.54-3.56 (3H, m), 3.95-4.18 (4H, m).

EXAMPLE 15

Preparation of Compound 15

Starting material 3-hydroxy-4-[(1,3-dimethyl-5-hydroxy)pyrazol-4-yl]cyclobutene-1,2-dione was synthesized in a similar manner to the method described in WO 01/44233.

To a mixed solvent of 2 ml of butanol and 1 ml of toluene, 1.04 g of 3-hydroxy-4-[(1,3-dimethyl-5-hydroxy)pyrazol-4-yl]cyclobutene-1,2-dione and 0.40 g of isobutylamine were added and the mixture was reacted at 100° C. to 110° C. for 5.0 hours. Then the reaction mixture was cooled to 20° C. to 30° C. and the precipitated yellow solid was collected by filtration to obtain Compound 15 (0.64 g).

$^1$H-NMR (CDCl$_3$) δppm: 1.03-1.08 (6H, m), 1.97-2.11 (1H, m), 2.43 (3H, s), 3.54 (3H, s), 3.58-3.62 (2H, m), 10.12 (1H, br).

EXAMPLE 16

Preparation of Compound 16

Starting material 3-hydroxy-4-[(5-hydroxy-1-methyl-3-trifluoromethyl)pyrazol-4-yl]cyclobutene-1,2-dione was synthesized in a similar manner to the method described in WO 01/44233.

To a mixed solvent of 2 ml of butanol and 1 ml of toluene, 1.00 g of 3-hydroxy-4-[(5-hydroxy-1-methyl-3-trifluoromethyl)pyrazol-4-yl]cyclobutene-1,2-dione and 0.36 g of piperidine were added and the mixture was reacted at 100° C. to 110° C. for 7.0 hours. Then, the reaction mixture was cooled to 20° C. to 30° C. and the precipitated yellow solid was collected by filtration to obtain Compound 16 (0.64 g).

$^1$H-NMR (CDCl$_3$) δppm: 1.76-1.90 (6H, m), 3.65-3.66 (3H, m), 4.06 (4H, s).

EXAMPLE 17

Preparation of Compound 17

Starting material 3-hydroxy-4-[(5-hydroxy-1-methyl-3-trifluoromethyl)pyrazol-4-yl]cyclobutene-1,2-dione was synthesized in a similar manner to the method described in WO 01/44233.

To a mixed solvent of 6 ml of butanol and 3 ml of toluene, 3.93 g of 3-hydroxy-4-[(5-hydroxy-1-methyl-3-trifluoromethyl)pyrazol-4-yl]cyclobutene-1,2-dione and 1.32 g of isobutylamine were added and the mixture was reacted at 100° C. to 110° C. for 13.0 hours. Then, the reaction mixture was cooled to 20° C. to 30° C. and the precipitated yellow solid was collected by filtration to obtain Compound 17 (1.69 g).

$^1$H-NMR (CDCl$_3$) δppm: 1.00-1.02 (2H, m), 1.04-1.07 (6H, m), 2.06-2.18 (1H, m), 3.67-3.71 (3H, m), 10.12 (1H, br).

TEST EXAMPLE 1

The absorption maximum wavelength (λmax) and logarithm of a molar extinction coefficient (log ε) of Compounds 1 to 16 in a chloroform solvent were measured (800 to 300 nm) using Spectorophotometer [UV-4000 (Hitachi Co., Ltd.)]. The results are shown in Table 1.

TABLE 1

Spectroscopic property of squarylium compounds

| Compound | Spectroscopic property (Chloroform solution) | |
|---|---|---|
| | λmax (nm) | logε |
| 1 | 412.5 | 4.8 |
| 2 | 411.0 | 4.8 |
| 3 | 411.0 | 4.8 |
| 4 | 439.5 | 4.7 |
| 5 | 410.5 | 4.7 |
| 6 | 407.5 | 4.8 |
| 7 | 406.0 | 4.8 |
| 8 | 414.0 | 4.9 |
| 9 | 407.5 | 4.8 |
| 10 | 403.0 | 4.8 |
| 11 | 412.0 | 4.8 |
| 12 | 422.0 | 4.7 |
| 13 | 404.0 | 4.7 |
| 14 | 399.5 | 4.7 |
| 15 | 407.0 | 4.5 |
| 16 | 397.5 | 4.5 |

TEST EXAMPLE 2

Each of a 1.0 percent by weight solution of Compound 1 or 5 dimethoxyethane, a 0.5 percent by weight solution of Compound 6 in dimethoxyethane or 0.5 percent by weight solution of Compound 9 or 11 in tetrahydrofuran and a 20 percent by weight solution of a polyester resin [VYLON 200 (a product of TOYOBO Co., Ltd.)] in dimethoxyethane were mixed at a ratio of 7:2, and the mixture was applied to a glass stubstrate using a spin coater, and dried to yield a coating film. The absorption maximum wavelength, the half maximum full-width, and the transmittance at 455 nm of the film were measured (800 to 300 nm) using Spectorophotometer [UV-4000 (Hitachi Co., Ltd.)]. The results are shown in Table 2.

TABLE 2

Absorption maximum wavelengths, half maximum full-widths, and transmittances at 455 nm of squarylium compounds in a film

| | Absorption maximum wavelength | Half maximum full-width | Transmittance at 455 nm |
|---|---|---|---|
| Compound 1 | 416.0 nm | 61.9 nm | 90% or more |
| Compound 5 | 410.0 nm | 57.1 nm | 90% or more |
| Compound 6 | 411.0 nm | 51.0 nm | 95% or more |
| Compound 9 | 411.5 nm | 54.0 nm | 90% or more |
| Compound 11 | 416.0 nm | 50.8 nm | 90% or more |

These results show that the filters for electronic display devices of the present invention can selectively shield the light having such a wavelength as to reduce the color purity, and can provide clear images.

INDUSTRIAL APPLICABILITY

The present invention can provide, for example, filters for electric display devices which improve colors of the electric display devices, etc.

What is claimed is:

1. A squarylium compound represented by Formula (Ic):

(Ic)

wherein $R^1$ and $R^2$ independently represent a hydrogen atom, an alkyl group optionally having substituent(s), an aralkyl group optionally having substituent(s), an aryl group optionally having substituent(s), or a heterocyclic group optionally having substituent(s); and
Y represents CH$_2$ or NH.

2. A squarylium compound according to claim 1, wherein $R^1$ is phenyl and $R^2$ is propyl.

3. A squarylium compound according to claim 2, wherein Y is CH$_2$.

4. A squarylium compound according to claim 2, wherein Y is NH.

* * * * *

UNITED STATES PATENT AND TRADEMARK OFFICE
CERTIFICATE OF CORRECTION

PATENT NO. : 7,521,562 B2 Page 1 of 2
APPLICATION NO. : 11/570355
DATED : April 21, 2009
INVENTOR(S) : Ikuo Shimizu et al.

It is certified that error appears in the above-identified patent and that said Letters Patent is hereby corrected as shown below:

ON THE TITLE PAGE AT ITEM (57) ABSTRACT

Line 10, "and" should read --and each--.

COLUMN 1

Line 14, "a" should be deleted; and
Line 22, "example" should read --examples--.

COLUMN 4

Line 4, "naphtylmethyl" should read --naphthylmethyl--.

COLUMN 6

Line 1, "which" should read --in which--.

COLUMN 7

Line 62, " 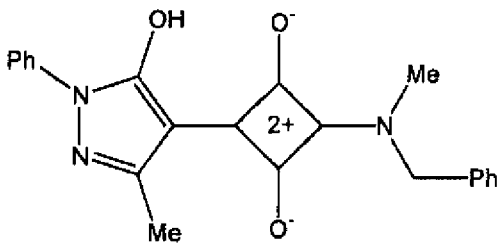 Compound 11" should read

-- 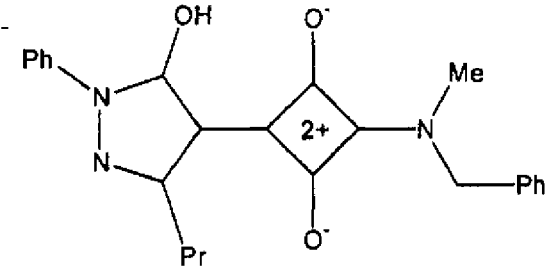 Compound 11--.

UNITED STATES PATENT AND TRADEMARK OFFICE
CERTIFICATE OF CORRECTION

PATENT NO. : 7,521,562 B2
APPLICATION NO. : 11/570355
DATED : April 21, 2009
INVENTOR(S) : Ikuo Shimizu et al.

It is certified that error appears in the above-identified patent and that said Letters Patent is hereby corrected as shown below:

COLUMN 15

Line 29, "Spectorophotometer" should read --Spectrophotometer--.

COLUMN 16

Line 8, "Spectorophotometer" should read --Spectrophotometer--.

Signed and Sealed this

Eleventh Day of August, 2009

David J. Kappos
*Director of the United States Patent and Trademark Office*